(12) United States Patent
Waldman et al.

(10) Patent No.: US 6,204,339 B1
(45) Date of Patent: *Mar. 20, 2001

US006204339B1

(54) ELASTOMERIC COMPOSITION COMPRISING A BLOCKED MERCAPTOSILANE COUPLING AGENT AND A DEBLOCKING AGENT

(75) Inventors: Bruce A. Waldman, Cortlandt Manor; Misty Weiyu Huang, New City; Richard W. Cruse, Yorktown Heights, all of NY (US)

(73) Assignee: Crompton Corporation, Greenwich, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/245,454

(22) Filed: Feb. 5, 1999

Related U.S. Application Data

(63) Continuation-in-part of application No. PCT/US98/17391, filed on Aug. 21, 1998.
(60) Provisional application No. 60/056,566, filed on Aug. 21, 1997.

(51) Int. Cl.[7] ............................... C08C 19/26; C08J 5/12; C08K 5/548
(52) U.S. Cl. ......................... 525/350; 525/342; 524/262; 524/265; 524/305
(58) Field of Search ................................... 525/350, 342; 524/262, 265, 302

(56) References Cited

U.S. PATENT DOCUMENTS

| | | |
|---|---|---|
| 3,502,704 | 3/1970 | McKeller et al. . |
| 3,692,812 | 9/1972 | Berger . |
| 3,922,436 | 11/1975 | Bell et al. . |
| 3,957,718 | 5/1976 | Pochert et al. . |
| 4,184,998 | 1/1980 | Shippy et al. . |
| 4,519,430 | 5/1985 | Ahmad et al. . |
| 4,820,751 | 4/1989 | Takeshita et al. . |

FOREIGN PATENT DOCUMENTS

| | | |
|---|---|---|
| 1008297 | 7/1997 | (AU) . |
| 2508931 | 9/1976 | (DE) . |
| 9817391 | 8/1998 | (WO) . |

OTHER PUBLICATIONS

Meeting Minutes, "Improved Performance of Silica and Carbon Black Filled Elastomers"—Dec. 17, 1998.
Preparation of Silylalkanethiols—XP–002084433—Jan. 1968.
Trialkoxysilylalkanethiols and Bis (trialkoxysilylaky) sulfides—XP–002084434—Aug. 1977.
Epxoy Resins Potting Compositions for Semiconductor Devices XP–002084435—Sep. 4, 1989.
Derwent Abstract —Japanese Patent No. 63270751, Nov. 8, 1988.

*Primary Examiner*—David W. Wu
*Assistant Examiner*—K L Egwim
(74) *Attorney, Agent, or Firm*—Shirley S. Ma

(57) ABSTRACT

This invention describes the use of blocked mercaptosilanes wherein the hydrogen atom of the mercaptan functionality has been substituted to manufacture coating, adhesive, sealant and elastomeric compositions. The blocked mercaptosilanes described are unique in that they allow the application of elastomers to substrates to proceed while remaining inert toward coupling to the catalyst. The coupling reactions of these blocked mercaptosilicon compounds are triggered by exposure to an appropriate deblocking agent.

20 Claims, No Drawings

ELASTOMERIC COMPOSITION COMPRISING A BLOCKED MERCAPTOSILANE COUPLING AGENT AND A DEBLOCKING AGENT

This case claims priority as a continuation in part of co-pending application PCT/US98/17391, filed Aug. 21, 1998, which in turn claims priority from U.S. patent application Ser. No. 06/056,566, filed on Aug. 21, 1997.

FIELD OF THE INVENTION

This invention relates to blocked mercapto silane coupling agents in coating, adhesive, sealant and elastomer applications ("CASE").

BACKGROUND

Mercaptosilanes have been known for use in tire applications to couple fillers to the rubber; however their utility in CASE has been limited due to the reactivity of the mercaptan functionality with catalysts which are used in CASE, i.e., the catalysts react with the mercaptan group thus de-activating the catalyst.

Specifically, the prior art discloses acylthioalkyl silanes, such as $CH_3C(=O)S(CH_2)_{1-3}Si(OR)_3$ [M. G. Voronkov et al. in Inst. Org. Khim., Irkutsk, Russia] and $HOC(=O)CH_2CH_2C(=O)S(CH_2)_3Si(OC_2H_5)_3$ [U.S. Pat. No. 3,922,436 to R. Bell et al.]. Japanese Patent 63270751A2 and DE 2508931 disclose the use of compounds represented by the general formula, $CH_2=C(CH_3)C(=O)S(CH_2)_{1-6}Si(OCH_3)_3$ in tire tread compositions, and adhesive compositions, respectively, but these compounds are not desirable because the unsaturation α,β to the carbonyl group of the thioester has the undesirable potential to polymerize during the compounding process, during storage or during the service life of the adhesive or coating.

Prior art by Yves Bomal and Olivier Durel, in Australian Patent AU-A-10082/97, discloses the use in rubber in conjunction with functionalized siloxanes of silanes of the structure represented by $R^1{}_nX_{3-n}Si—(Alk)_m(Ar)_p—S(C=O)—R$ where $R^1$ is phenyl or alkyl; X is halogen, alkoxy, cycloalkoxy, acyloxy, or OH; Alk is alkyl; Ar is aryl; R is alkyl, alkenyl, or aryl; n is 0 to 2; and m and p are each 0 or 1, but not both zero.

U.S. Pat. No. 3,922,436 to Bell disclose a mercaptan/acid anhydride adduct as coupling agents for filled plastics, but there is no teaching to de-block the mercaptan group. U.S. Pat. No. 4,820,751 discloses certain blocked mercaptosilane for tires but again does not disclose any de-blocking of such silanes. U.S. Pat. No. 4,519,430 to Ahamd et al. and U.S. Pat. No. 4,184,998 to Shippy et al. disclose the blocking of a mercaptosilane with an isocyanate to form a solid which is added to a tire composition, which mercaptan reacts into the tire during heating, which could happen at any time during processing since this a thermal mechanism.

There remains a need for effective latent coupling agents which exhibit the advantages of mercaptosilanes without exhibiting the disadvantages such as described herein.

SUMMARY OF THE INVENTION

The present invention relates to compositions of an elastomer with an intrinsic or extrinsic crosslinker, a cure catalyst and a blocked mercaptosilane which are used as an adhesive, sealant or coating on a substrate. Methods of manufacturing such adhesive, sealants or coatings also are disclosed wherein the mercaptosilane is de-blocked during or after the curing of the composition.

DETAILED DESCRIPTION OF THE INVENTION

The latent mercaptosilanes have a blocking group on the mercaptan. This prevents the mercapto group from participating adversely in undesirable side reactions such as deactivation of cure catalysts, including organometallics, such as organotins. Undesired reactions of the mercapto group are slowed or prevented entirely until the blocking group is removed. As the blocking group is removed after application of a sealant or other system containing the mercaptosilanes, the desired reaction can occur or accelerate. If cure catalysts are affected at this point, it can be less critical since initial curing already has begun under the influences of the undisturbed catalyst. The deblocking mercapto group also can participate more readily in the curing reaction of the polymer system, in the normal mode of silane coupling agents.

COMPOSITION

The CASE compositions of the present invention are comprised of (a) an elastomer; (b) an intrinsic or extrinsic crosslinker; (c) a metallic or organometallic cure catalyst with a metal selected from the periodic groups VIIB, VIII, IB IIB, IIIA and IVA ; and (d) a blocked mercaptosilanes, which is deblocked with a (e) deblocking agent while the composition is on a (f) substrate. Standard excipients may also be included in the compositions.

Elastomer

The elastomer may be organic or inorganic polymers, such acrylates, methacrylates, vinyls, urethanes, polyester, polysiloxane, epoxides, polyolefins, polyureas, and polyols. Preferred for use herein are isocyanate or silane terminated urethanes and polyols.

Crosslinker

The crosslinker is a compound which has at least two functionalities which will react with the elastomer so that upon curing, the crosslinker will crosslink the elastomer. Examples of extrinsic (i.e., separate) crosslinkers are organofunctional silanes, vinyl functionalized siloxanes, isocyanates, or epoxides. Moreover, the crosslinking functionality may be part of the elastomer compound (i.e., intrinsic to the elastomer), e.g., an isocyanate end-capped polyol, an alkoxy silane terminated polyol or urethane or a silylated polyethylene (e.g., SI-LINK (Union Carbide) and MS Polymer (Kaneka)).

Examples of alkoxy silanes which may be used are γ-aminopropyltrimethoxy silane, bis(trimethoxysilylpropyl)amine; N-phenyl-γ-aminopropyltrimethoxysilane; γ-glycidoxypropyl triethoxy silane; 3,4 epxoycyclohexylpropyl trimethoxysilane; γ-isocyanatopropyl triethoxysilane; vinyltrimethoxysilane, methacryloxypropyl triethoxysilane, The isocyanates or blocked isocyanates which may be used are methylene di-isocyanate (MDI), toluene di-isocyanate (TDI), 2,6-toluenediisocyanate, isophorone diisocyanate, dicyclohexylmethane-4,4'-diisocyanate, various liquid diphenyl methane-diisocyanates containing mixtures of 2,4- and 4,4' isomers, DesmodurN® and the like and mixtures thereof.

The crosslinker should be present at 0.1 to 20 parts per hundred of elastomer, more preferably 1 to 10 parts per hundred.

Cure Catalyst

The cure catalyst is intended to cure the elastomer to the crosslinker and the crosslinkers to each other and the alkoxy functionality of the mercaptosilane. Examples of such cure catalysts are organotins, platinum, palladium and other catalysts from the periodic groups VIIB, VIII, IB, IIB IIIA and IVA. Organotins are preferred.

The catalyst should be present at 0.001 to 2 parts per hundred of the elastomer, preferably 0.01 to 1.0 parts per hundred elastomer.

Substrate

Inorganic substrates containing elements capable of complexation with the -SH group should be used. Such substrates might contain Zn, Cu, Pb, Bi and Sn as examples. The substrates may be glass, ceramics, galvanized metals, and plastics. Specific substrates include windscreens, aluminum, steel, and copper. Some specific applications include as an adhesive between a metalloceramic and a paint or coating and between copper wiring and a circuit board. More specifically an application of note is to bind the metalloceramic frit of a windscreen to the painted surface of the vehicle (e.g., boat, automobile, airplane, etc.).

Blocked Mercaptosilanes

The blocked mercaptosilanes are mercapto silanes wherein the hydrogen on the sulfur atom has been replaced by another labile group, but not by another sulfur atom. Polysulfide silanes, such as SILQUEST silanes A-1289 and A-1589 from Witco Corp., are not considered herein to be blocked mercaptosilanes. These blocked mercaptosilanes can be represented by the Formulae (1–2):

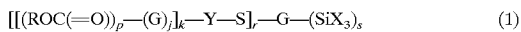  (1)

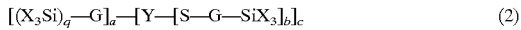  (2)

wherein

Y is a polyvalent species $(Q)_zA(=E)$, wherein Q, A, E and z are as below. Y preferably is selected from the group consisting of —C(=NR)—; —SC(=O)—; (—NR)C(=O)—; (—NR)C(=S)—; —OC(=O)—; —OC(=S)—; —C(=O)—; —SC(=S)—; —C(=S)—; each wherein the atom (A) attached to the unsaturated heteroatom (E) is attached to the sulfur, which in turn is linked via a group G to the silicon atom;

each R is chosen independently from hydrogen, straight, cyclic or branched alkyl that may or may not contain unsaturation, alkenyl groups, aryl groups, and aralkyl groups, with each R containing from 1 to 18 carbon atoms;

each G is independently a monovalent or polyvalent group derived by substitution of alkyl, alkenyl, aryl or aralkyl wherein G can contain from 1 to 18 carbon atoms, with the proviso that preferably G is not such that the silane would contain an α,β-unsaturated carbonyl including a carbon-carbon double bond next to the thiocarbonyl group, and if G is univalent (i.e., if p =0), G can be a hydrogen atom;

X is independently a group selected from the group consisting of —Cl, —Br, RO—, RC(=O)O—, $R_2$C=NO—, $R_2$NO— or $R_2$N—, —R, —$(OSiR_2)_t$ $(OSiR_3)$ wherein each R and G is above and at least one X is not —R;

Q is oxygen, sulfur or (—NR—);

A is carbon, sulfur, phosphorus, or sulfonyl;

E is oxygen, sulfur or NR;

p is 0 to 5; r is 1 to 3; z is 0 to 2; q is 0 to 6; a is 0 to 7; b is 1 to 3; j is 0 to 1, but it may be 0 only if p is 1, c is 1 to 6, preferably 1 to 4; t is 0 to 5; s is 1 to 3; k is 1 to 2, with the provisos that (A) if A is carbon, sulfur or sulfonyl, then (i) a+b=2 and (ii) k=1; (B) if A is phosphorus, then a+b=3 unless both (i) c>1 and (ii) b=1, in which case a=c+1; and (C) if A is phosphorus, then k is 2.

As used herein, "alkyl" includes straight, branched and cyclic alkyl groups, and "alkenyl" includes straight, branched and cyclic alkenyl groups containing one or more carbon-carbon double bonds. Specific alkyls include methyl, ethyl, propyl, isobutyl, and specific aralkyls include phenyl, tolyl and phenethyl. As used herein, "cyclic alkyl" or "cyclic alkenyl" also includes bicyclic and higher cyclic structures, as well as cyclic structures further substituted with alkyl groups. Representative examples include norbornyl, norbornenyl, ethylnorbornyl, ethylnorbornenyl, ethylcyclohexyl, ethylcyclohexenyl, and cyclohexylcyclohexyl.

Representative examples of the functional groups (-YS-) present in the silanes of the present invention include thiocarboxylate ester, —C(=O)—S— (any silane with this functional group is a "thiocarboxylate ester silane"); dithiocarboxylate, —C(=S)—S— (any silane with this functional group is a "dithiocarboxylate ester silane"); thiocarbonate ester, —O—C(=O)—S— (any silane with this functional group is a "thiocarbonate ester silane"); dithiocarbonate ester, —S—C(=O)—S— and —O—C(=S)—S—(any silane with this functional group is a "dithiocarbonate ester silane"); trithiocarbonate ester, —S—C(=S)—S— (any silane with this functional group is a "trithiocarbonate ester silane"); and dithiocarbamate ester, N—C(=S)—S— (any silane with this functional group is a "dithiocarbamate ester silane").

Another structure is of the form $X_3SiGSC(=O)TC(=O)SGSiX_3$ wherein T is a divalent hydrocarbon. Examples of T include —$(CH_2)_n$— wherein n is 1 to 12, diethylene cyclohexane, 1,2,4-triethylene cyclohexane, and diethylene benzene. It is preferred that the sum of the carbon atoms within the T groups within the molecule are from 3 to 18, more preferably 6 to 14. This amount of carbon in the blocked mercaptosilane facilitates the dispersion into the organic polymers.

Preferable R groups are alkyls of $C_1$ to $C_4$ and H.

Specific examples of X are methoxy, ethoxy, isobutoxy, propoxy, isopropoxy, acetoxy and oximato. Methoxy, acetoxy and ethoxy are preferred. At least one X must be reactive (i.e., hydrolyzable).

Preferred embodiments are wherein p is 0 to 2; X is RO— or RC(=O)O—; R are hydrogen, phenyl, isopropyl, cyclohexyl, or isobutyl; G is a substituted phenyl or substituted straight chain alkyl of $C_2$ to $C_{12}$. The most preferred embodiments include those wherein p is zero; X is ethoxy and G is a $C_3$—$C_{12}$ alkyl derivative. A subset of this is mono-carboxylic acid blocked mercaptosilanes are preferred as well, i.e., of formula I wherein p=0, r=1, s=1, k=1, and j=1, i.e., G—C(=O)S—G—(SiX_3).

Representative examples of the silanes for use herein include 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate;

3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpenyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctoate; 3-triethoxysilyl-1-propyl thiopalmitate; 3-triethoxysilyl-1-propyl thiooctoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; 2-methyldiacetoxysilyl-1-ethyl thioacetate; 2-triacetoxysilyl-1-ethyl thioacetate; 1-methyldiacetoxysilyl-1-ethyl thioacetate; and 1-triacetoxysilyl-1-ethyl thioacetate.

Mixtures of various blocked mercaptosilanes may be used, including wherein synthetic methods result in a distribution of various silanes or where mixes of blocked mercaptosilanes are used for their various blocking or leaving functionalities. Moreover, it is understood that the partial hydrolyzates of these blocked mercaptosilanes (i.e., blocked mercaptosiloxanes) may also be encompassed by the blocked mercaptosilanes herein, in that these partial hydrolyzates will be a side product of most methods of manufacture of the blocked mercaptosilane or can occur upon storage of the blocked mercaptosilane, especially in humid conditions.

The manufacture of the silanes above is taught in PCT/US98/17391; U.S. Pat. No. 3,692,812; Gornowicz, G., "Preparation of Silylalkanethiols", *J. Org. Chem.*, Vol. 33, No. Jul. 7, 1968; Vorkonov, M. G., et al., "Trialkoxysilylalkanethiols and Bis(trialkoxysilylakyl)sulfides", *Izvestiya Akademii Nauk SSSR*, Seriya Khimicheskeya, No. 8, pp. 1849–51, August 1977, which are incorporated herein by reference.

The mercaptosilane should be present at 0.01 to 5 parts per hundred elastomer, more preferably 0.1 to 2 parts per hundred.

Deblocking Agents

In most cases the deblocking agent will simply be environmental moisture present either from the atmosphere or present on the substrate. If alcohol or water are present (as is common) in the mixture, a catalyst (e.g., tertiary amines, Lewis acids or thiols) may be used to initiate and promote the loss of the blocking group by hydrolysis or alcoholysis to liberate the corresponding mercaptosilane. Alternatively, the deblocking agent may be a nucleophile containing a hydrogen atom sufficiently labile such that hydrogen atom could be transferred to the site of the original blocking group to form the mercaptosilane. Thus, with a blocking group acceptor molecule, an exchange of hydrogen from the nucleophile would occur with the blocking group of the blocked mercaptosilane to form the mercaptosilane and the corresponding derivative of the nucleophile containing the original blocking group.

The deblocking agent may be added at quantities ranging from about 0.1 to about 5 pph elastomer; more preferably in the range of from 0.5 to 3 pph elastomer. The initially substantially inactive (from the standpoint of coupling to the catalyst and substrate) blocked mercaptosilane is substantially converted at the desired point to the active mercaptosilane. It is noted that partial amounts of the nucleophile may be used (i.e., a stoichiometric deficiency), if one were to only deblock part of the blocked mercaptosilane to control the degree of adhesion of a specific formulation.

Examples of nucleophiles suitable as deblocking agents would include any primary or secondary amines, or amines containing C=N double bonds, such as imines or guanidines; with the proviso that said amine contains at least one N-H (nitrogen-hydrogen) bond. Numerous specific examples of guanidines, amines, and imines well known in the art, which are useful as components in curatives for rubber, are cited in *Rubber Chemicals*; J. Van Alphen; Plastics and Rubber Research Institute TNO, Delft, Holland; 1973. Some examples include N,N'-diphenylguanidine, N,N',N"-triphenylguanidine, N, N'-di-ortho-tolylguanidine, ortho-biguanide, hexamethylenetetramine, cyclohexylethylamine, dibutylamine, and 4,4'-diaminodiphenylmethane. Any general acid catalysts used to transesterify esters, such as Bronsted or Lewis acids, could be used as catalysts.

Excipients

Standard excipients may be used, such as fillers (titanium dioxide), antioxidants, extenders (calcium carbonate), UV inhibitors, thixotropes, rheology control agents, surfactants and pigments.

Representative examples of suitable filler materials include metal oxides, such as silica (pyrogenic and precipitated), titanium dioxide, calcium carbonate, aluminosilicate and alumina, siliceous materials including clays and talc, and carbon black. The fillers may be hydrated or in anhydrous form, though the anhydrous form is preferred so as not to deblock prematurely the mercaptosilane.

Process of Use

The blends of the elastomer crosslinker, catalyst, and silane may be done in any fashion. The blocking group substantially prevents the silane from deactivating the cure catalyst to a degree sufficient to make it catalytically ineffective during the blending of the composition. These compositions may be set up as one pack systems with all of these ingredients being mixed together at the same time or as two part systems wherein the catalyst or other ingredients is kept separate from the crosslinker or other ingredients until the time of application. Some specific CASE systems are a polyol endcapped urethane (which may be partially or fully endcapped with a silane) with a mercaptosilane and tin catalyst; an isocyanate crosslinker, a polyol, a tin catalyst and the latent mercaptosilane; or a silanol terminated siloxane, tin catalyst and a latent mercaptosilane.

When reaction of the CASE mixture to couple the elastomer to the substrate (or alternatively, to deactivate the cure catalyst) is desired, a deblocking agent is added to the mixture to deblock the blocked mercaptosilane. Such deblocking agent should be added just before the mixture is applied to the substrate, as the mixture is applied to the substrate or after the mixture has been applied to the substrate. If an adhesive utility is contemplated, contact should be made with the second substrate as or before the decoupling agent is added. In many cases a suitable deblocking agent is environmental moisture.

The deblocking agent could be added in a curative package with the cure catalyst or, alternatively, at any other stage in the curing process as a single component. In such cases, the relative rate of reaction between deblocking and crosslinking will make a difference as to the strength of adhesion in light of the a fast deblocking could result in deactivation of the catalyst before complete crosslinking. In the cases cited above, the compositions simply may be exposed to moist air which would result in water being the de-blocking agent. Pressure, heating and UV radiation may be used to accelerate the cure of mercaptosilane and/or the crosslinker.

Alternatively, this process has a specific utility in CASE systems using an isocyanate cure and tin catalysts. In such systems, the tin catalysts stay active after cure of the CASE systems. When such systems are later exposed to heat and moisture they may tend to "revert" to lower molecular weight species. The latent mercaptosilanes, after de-blocking, eventually will deactivate the residual tin catalyst, forming a much less reactive mercaptotin. The result is less tendency for reversion of the cured CASE. In such cases the mercaptosilane may not couple to the substrate, but simply act as a deactivation agent.

All references cited herein are incorporated herein as they are relevant to the present invention.

The invention may be better understood by reference to the following examples in which the parts and percentages are by weight unless otherwise indicated.

EXAMPLES

Cure speed of the prepolymer with different mercaptosilanes

Prepolymer sample for measuring cure speed was prepared from the ANDUR SEAL 221-16, a silane end-capped polyurethane prepolymer of average molecular weight of about 7000–8000, which both ends are capped by phenylaminopropyltrimethoxysilane, provided by Anderson Development Company. Into a small aluminum pan was placed 10 grams of the silylated urethane prepolymer, 0.1 gram of FOMREZ SUL 11A (a liquid dibutyltin oxide, Witco Corp.), and 0.3 gram of the experimental latent mercaptosilane. The mixture was manually stirred by a spatula, and cured at ambient condition. The tack free time was checked by finger touch every 15 minutes. Comparison of the curing speed of those prepolymers with different latent mercaptosilanes was listed in Table I.

TABLE 1

Curing Speed of the Silane Containing Prepolymer

| | Silane | Tack Free Time (minutes) |
|---|---|---|
| Sample 1 | 2-(acetylthio)-1-trimethoxysilane | 252 |
| Sample 2 | 8-(acetylthio)-1-octyltriethoxysilane | 120 |
| Sample 3 | 2-(acetylthio)-1-ethylmethyldimethoxysilane | 135 |
| Sample 4 | 2-(acetylthionorbornyl)-5-ethyltrimethoxysilane | 250 |
| Sample 5 | 3-(acetylthio)-1-propylmethyldiacetoxysilane | 420 |
| Comparative sample 1 | γ-mercaptopropyltrimethoxysilane (Silquest ® A189 silane) | >1140 |
| Comparative sample 2 | N-β-(aminoethyl)-γ-aminopropyltrimethoxysiane (Silquest ® A1120 silane) | 55 |

PREPARATION OF URETHANE SEALANTS

TABLE 2

Formulation of the Polyurethane Sealant

| Product Name | Description | Source | Weight (g) |
|---|---|---|---|
| Andur Seal 221-16 | Silane Endcapped Polyurethane | Anderson Dvlpmnt Co. | 250 |
| SANTICIZER 160 | Diisodecylphthalate | Monsanto | 100 |
| SILQUEST ® A-171 SILANE | Desiccant | Witco Co. | 5 |
| ULTRA-PFLEX | $CaCO_3$ | Pfizer | 150 |
| HI-PFLEX | $CaCO_3$ | Pfizer | 100 |
| TINUVIN ® 213 | UV stabilizer | Ciba Geigy | 2.5 |
| TINUVIN ® 622LD | UV stabiiizer | Ciba Geigy | 2.5 |
| TI PURE - 960-28 | $TiO_2$ | DuPont | 7.5 |
| CAB-O-SIL ® TS-720 | $SiO_2$ | Cabot | 15 |
| Latent Mercaptosilane | Adhesion Promoter | Witco Co. | 3.75 |
| FOMREZ SUL 11 A | Organotin | Witco Co. | 0.5 |

To ensure low water content all fillers were pre-dried for a minimum of 24 hours at 120° C. prior to use. Into a one quart double planetary mixer was placed with the above ANDUR SEAL 221-16, A-171 Silane, DIDP, $CaCO_3$, $TiO_2$ and UV stabilizers. The blend was mixed at 40 rpm for 120 minutes at 50° C. under nitrogen. $SiO_2$ was added and the mixture was stirred for another 15 minutes before adding 3.75 grams of 2-(acetylthio)-1-trimethoxysilane and SUL 11A. The mixture was stirred for an additional 20 minutes under full vacuum. The finished sealant was removed and packaged in an aluminum foil lined cartridge.

In experiments 2–6 and Comparative Examples 1 and 2, the silane of Experiment 1 was replaced with the following silanes.

Experiment 2—8-(acetylthio)-1-octyltriethoxysilane;

Experiment 3—(acetylthio)-1-ethylmethyldimethoxysilane;

Experiment 4—2-(acetylthionorbornyl)-5-ethyltrimethoxysilane;

Experiment 5—3-(acetylthio)-1-propylmethyldiacetoxysilane;

Experiment 6—a mixture of 1.875 gram of 2-(acetylthio)-1-trimethoxysilane and 1.875 gram of N-(β-(aminoethyl)-(γ-aminopropyltrimethoxysilane;

Comparative 1—(γ-mercaptopropyltrimethoxysilane;

Comparative 2—N-(β-(aminoethyl)-(γ-aminopropyltrimethoxysilane.

Sample Preparation for Evaluation of Tin Catalyst: In experiments 7–10, the SUL 11A was replaced with the following catalysts—

Experiment 7—0.158 gm of FOMREZ SUL 4, dibutyltin dilaurate;

Experiment 8—0.158 gm of dioctyltin diacetate from Witco;

Experiment 9—0.158 gm of NEOSTANN U-220, dibutyltin bis(acetylacetonate); and

Experiment 10—0.158 gm of FASCAT 4200, an organic tin catalyst from Atochem.

Adhesion-in-peel Test

The ceramic frit substrates, with or without lead, were provided by Libby Owens Ford. All test substrates were thoroughly cleaned by isopropanol, detergent (0.1% solution) and rinsed by deionized water. The cleaned substrates were allowed to air dry prior use. The adhesion-in-peel testing was conducted in accordance to the ASTM C 794 procedure. The experimental sealant was spread over ⅔ of the substrate coupon to a depth of approximately 1/16" (15 mm). The sealant was then covered with a aluminum screen (30 mesh) which was covered with an additional 1/16" (15mm) layer of the sealant. Specimens were cured for a 21 days according the following schedule: 7 days at 23° C. and 50% RH; 7 days at 38° C. and 95% RH; 7 days at 23° C. and 50% RH. The cured specimens were immersed into water for 7 days prior to test. The 180° peel strength was measured on an Instron.

Mechanical Properties Test

Mechanical properties were evaluated using ASTM specifications. Tensile strength, elongation, modulus (ASTM D 412), Shore A hardness (ASTM C 661) and tear resistance (ASTM D 624) data were obtained on samples cured according to the following schedule: 3 days at 23° C. and 50% RH followed by an additional 4 days at 50° C.

TABLE 3

Adhesion to Substrates

| | Glass | | Ceramic Frit w/o Pb | | Ceramic Frit w/ Pb | |
|---|---|---|---|---|---|---|
| | Peel Strength (N/mm) | Failure | Peel Strength (N/mm) | Failure | Peel Strength (N/mm) | Failure |
| Example 1 | 4.08 | 75% CF | 3.90 | 100% CF | 6.23 | 100% CF |
| Example 2 | 4.90 | 100% CF | 4.32 | 100% CF | 3.50 | 100% CF |
| Example 3 | 5.93 | 100% CF | 4.76 | 100% CF | 3.69 | 100% CF |
| Example 4 | 5.34 | 100% CF | 4.57 | 100% CF | 4.36 | 100% CF |
| Example 5 | 2.99 | 100% CF | 2.03 | 98% AF | 2.96 | 100% CF |
| Example 6* | 0.82 | 100% CF | 0.75 | 100% CF | 0.93 | 100% CF |
| Compare 1* | 0.14 | 100% AF | 0.18 | 100% CF | 0.11 | 100% CF |
| Compare 2 | 3.08 | 100% CF | 0.79 | 100% AF | 3.68 | 100% CF |

*The samples reacted slowly and could not be fully cured after at least three weeks.
CF — Cohesive failure; AF — Adhesive failure

TABLE 4

Mechanical Properties

| | Tensile Strength (MPa) | Youngs Modulus (MPa) | Elongation (100%) | Tear Resistance (N/mm) | Shore A Hardness |
|---|---|---|---|---|---|
| Example 1 | 1.738 | 0.476 | 598 | 6.86 | 31 |
| Example 2 | 1.765 | 0.703 | 455 | 7.44 | 36 |
| Example 3 | 1.310 | 0.572 | 445 | 7.35 | 33 |
| Example 4 | 1.600 | 0.552 | 553 | 7.63 | 28 |
| Example 5 | 1.531 | 0.765 | 442 | 6.79 | 35 |
| Example 6* | 0.200 | 0.283 | 156 | 1.58 | 5 |
| Compare 1* | 0.179 | 0.103 | 244 | 1.23 | 11 |
| Compare 2 | 1.455 | 1.110 | 194 | 4.34 | 46 |

*The samples reacted slowly and could not be fully cured after at least three weeks.

TABLE 5

Effect of Catalyst on Adhesion of the Sealant

| | Glass | | Ceramic Frit w/o Pb | | Ceramic Frit w/ Pb | |
|---|---|---|---|---|---|---|
| | Peel Strength (N/mm) | Failure | Peel Strength (N/mm) | Failure | Peel Strength (N/mm) | Failure |
| Example 1 | 4.08 | 75% CF | 3.90 | 100% CF | 6.23 | 100% CF |
| Example 7 | 2.57 | 90% AF | 3.57 | 100% CF | 4.53 | 100% CF |
| Example 8 | 4.59 | 100% CF | 3.20 | 100% CF | 5.15 | 100% CF |
| Example 9 | 4.49 | 100% CF | 3.40 | 100% CF | 3.45 | 100% CF |
| Example 10 | 3.89 | 100% CF | 2.77 | 100% CF | 3.40 | 100% CF |

TABLE 6

Effect of Catalyst on Properties of the Sealants

| | Tensile Strength (MPa) | Youngs Modulus (MPa) | Elongation (100%) | Tear Resistance (N/mm) | Shore A Hardness |
|---|---|---|---|---|---|
| Example 1 | 1.738 | 0.476 | 598 | 6.86 | 31 |
| Example 7 | 0.800 | 0.131 | 823 | 3.43 | 14 |
| Example 8 | 1.027 | 0.228 | 614 | 4.80 | 20 |
| Example 9 | 0.924 | 0.207 | 607 | 4.53 | 22 |
| Example 10 | 1.703 | 0.393 | 630 | 7.42 | 28 |

The sealants contained latent mercaptosilanes cured faster than that of contained conventional mercaptosilanes. All the latent mercaptosilanes gave sealants excellent adhesion to glass and ceramic frits with or without lead, while aminosilane did not adhere to the frit without lead.

What is claimed is:

1. A composition comprising:
   a. an elastomer;
   b. a crosslinker, either intrinsic or extrinsic to the elastomer;
   c. a metallo or organometallic cure catalyst;
   d. a blocked mercaptosilane;
   e. a deblocking agent; and
   f. a substrate.

2. A composition according to claim 1 wherein the blocked mercaptosilane is represented by Formulae 1 or 2:

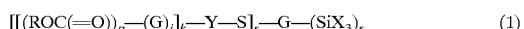

$$[[(ROC(=O))_p\text{—}(G)_j]_k\text{—}Y\text{—}S]_r\text{—}G\text{—}(SiX_3)_s \quad (1)$$

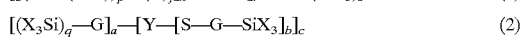

$$[(X_3Si)_q\text{—}G]_a\text{—}[Y\text{—}[S\text{—}G\text{—}SiX_3]_b]_c \quad (2)$$

wherein

Y is a polyvalent species $(Q)_zA(=E)$, wherein the atom (A) attached to the unsaturated heteroatom (E) is attached to the sulfur, which in turn is linked via a group G to the silicon atom;

each R is chosen independently from hydrogen, straight, cyclic or branched alkyl that may or may not contain unsaturation, alkenyl groups, aryl groups, and aralkyl groups, with each R containing from 1 to 18 carbon atoms;

each G is independently a monovalent or polyvalent group derived by substitution of alkyl, alkenyl, aryl or aralkyl, wherein G can contain from 1 to 18 carbon atoms;

X is independently selected from the group consisting of —Cl, —Br, RO—, RC(=O)O—, R$_2$C=NO—, R$_2$NO—, R$_2$N—, —R, and —(OSiR$_2$)$_t$(OSiR$_3$) wherein each R and G is as above and at least one X is not —R;

Q is oxygen, sulfur or (—NR—);

A is carbon, sulfur, phosphorus, or sulfonyl;

E is oxygen, sulfur or NR;

p is 0 to 5; r is 1 to 3; z is 0 to 2; q is 0 to 6; a is 0 to 7; b is 1 to 3; j is 0 to 1, but it may be 0 only if p is 1, c is 1 to 6; t is 0 to 5; s is 1 to 3; k is 1 to 2, with the provisos that (A) if A is carbon, sulfur or sulfonyl, then (i) a+b=2 and (ii) k=1; (B) if A is phosphorus, then a+b=3 unless both (i) c>1 and (ii) b=1, in which case a=c+1; and (C) if A is phosphorus, then k is 2.

3. A composition according to claim 1 wherein the elastomer is selected from the group consisting of: acrylates, methacrylates, vinyls, urethanes, polyesters, polysiloxanes, epoxides, polyolefins, polyureas, and polyols.

4. A composition according to claim 1 wherein the crosslinker is extrinsic and selected from the group consisting of organofunctional silanes, vinyl functionalized siloxanes, isocyanates, and epoxides.

5. A composition according to claim 1 wherein the crosslinker is intrinsic to the elastomer and the elastomer is selected from the group consisting of: an isocyanate end-capped polyol, an alkoxy silane terminated polyol, an alkoxy silane terminated urethane, and a silylated polyethylene.

6. A composition according to claim 5 wherein the mercaptosilane is of the structure:

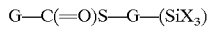

wherein each G is independently a monovalent or polyvalent group derived by substitution of alkyl, alkenyl, aryl or aralkyl, wherein G can contain from 1 to 18 carbon atoms and X is independently selected from the group consisting of —Cl, —Br, RO—, RC(=O)O—, R$_2$C=NO—, R$_2$NO—, R$_2$N—, —R, and —(OSiR$_2$)$_t$(OSiR$_3$), wherein each R and G is as above and at least one X is not —R.

7. A composition according to claim 6 wherein the cure catalyst is an organotin.

8. A composition according to claim 7 wherein the deblocking agent is water.

9. A composition according to claim 1 wherein the crosslinker is an alkonysilane, the catalyst is an organotin and the blocked mercaptosilane is of the structure G—C(=O)S—G—(SiX$_3$) wherein each G is independently a monovalent or polyvalent group derived by substitution of alkyl, alkenyl, aryl or aralkyl, wherein G can contain from 1 to 18 carbon atoms and X is independently selected from the group consisting of —Cl, —Br, RO—, RC(=O)O—, R$_2$C=NO—, R$_2$NO—, R$_2$N—, —R, and —(OSiR$_2$)$_t$(OSiR$_3$), wherein each R is chosen independently from hydrogen, straight, cyclic or barnched alkyl that may or may not contain unsaturation, alkenyl groups, aryl groups, and aralkly groups, G is as above and at least one X is not —R.

10. A process comprising:
   a. mixing an elastomer, an intrinsic or extrinsic crosslinker, a cure catalyst, and a blocked mercaptosilane;
   b. applying the mixture of step (a) to a substrate;
   c. deblocking the mercaptosilane, either as part step (b) or after step (b); and
   d. allowing the mixture to cure.

11. A process according to claim 10 wherein the elastomer is selected from the group consisting of acrylates, methacrylates, vinyls, urethanes, polyester, polysiloxane, epoxides, polyolefins, polyureas, and polyols; and the crosslinker is extrinsic and selected from the group consisting of organofunctional silanes, isocyanates, and epoxides.

12. A process according to claim 10 wherein the crosslinker is intrinsic and the elastomer is selected from the group consisting of: an isocyanate end-capped polyol, an alkoxy silane terminated polyol, an alkoxy silane terminated urethane, and a silylated polyethylene.

13. A process according to claim 10 wherein the catalyst is an organotin.

14. A process according to claim 10 wherein the crosslinker, elastomer and mercaptosilane are mixed together and then mixed with the cure catalyst prior to application to the substrate.

15. A process according to claim 10 wherein the silane is of the structure G—C(=O)S—G—(SiX$_3$) wherein each G is independently a monovalent or polyvalent group derived by substitution of alkyl, alkenyl, aryl or aralkyl, wherein G can contain from 1 to 18 carbon atoms and X is independently selected from the group consisting of —Cl, —Br, RO—, RC(=O)O—, R$_2$C=NO—, R$_2$NO—, R$_2$N—, —R, and —(OSiR$_2$)$_t$(OSiR$_3$), wherein each R is chosen independently from hydrogen, straight, cyclic or barnched alkyl that may or may not contain unsaturation, alkenyl groups, aryl groups, and aralkly groups, G is as above and at least one X is not —R.

16. A process according to claim 15 wherein the crosslinker is an alkoxysilane.

17. A process according to claim 16 wherein the deblocking agent is water.

18. A process according to claim 17 wherein the catalyst is an organotin.

19. A process according to claim 18 wherein the elastomer is selected from the group consisting of acrylates, methacrylates, vinyls, urethanes, polyester, polysiloxane, epoxides, polyolefins, polyureas and polyols.

20. A process according to claim 15 wherein crosslinker is intrinsic and the elastomer is selected from the group consisting of: an isocyanate end-capped polyol, an alkoxy silane terminated polyol, an alkoxy silane terminated urethane, silylated polyethylene and a silylated latex.

* * * * *